United States Patent
Amr et al.

(10) Patent No.: US 9,975,917 B1
(45) Date of Patent: May 22, 2018

(54) PENTACYCLIC TRITERPENOIDAL DERIVATIVES

(71) Applicant: KING SAUD UNIVERSITY, Riyadh (SA)

(72) Inventors: Abd El-Galil E. Amr, Riyadh (SA); Mohamed A. Al-Omar, Riyadh (SA); Ahmed M. Naglah, Riyadh (SA)

(73) Assignee: KING SAUD UNIVERSITY, Riyadh (SA)

( * ) Notice: Subject to any disclaimer, the term of this patent is extended or adjusted under 35 U.S.C. 154(b) by 0 days. days.

(21) Appl. No.: 15/710,721

(22) Filed: Sep. 20, 2017

(51) Int. Cl.
*A61K 31/56* (2006.01)
*C07J 63/00* (2006.01)

(52) U.S. Cl.
CPC .............. *C07J 63/008* (2013.01); *A61K 31/56* (2013.01)

(58) Field of Classification Search
CPC ..... A61K 31/56; A61K 31/426; A61K 31/337
See application file for complete search history.

(56) References Cited

U.S. PATENT DOCUMENTS

| | | | |
|---|---|---|---|
| 7,195,790 B2 | 3/2007 | Zang et al. | |
| 8,226,989 B2 | 7/2012 | Gokaraju et al. | |
| 8,343,554 B2 | 1/2013 | Bombardelli | |
| 8,748,598 B2 | 6/2014 | Gokaraju et al. | |
| 8,975,228 B2 | 3/2015 | Ammon | |
| 2007/0253943 A1 | 11/2007 | Altunkaya | |
| 2009/0298938 A1* | 12/2009 | Qazi | A61K 31/19 514/557 |
| 2010/0166670 A1 | 7/2010 | Ammon et al. | |

FOREIGN PATENT DOCUMENTS

| | | |
|---|---|---|
| DE | 100 53 056 A1 | 4/2002 |
| EP | 0552657 A1 | 7/1993 |
| WO | 0215916 A1 | 2/2002 |
| WO | 02/085921 A2 | 10/2002 |
| WO | 2006/022762 A1 | 3/2006 |

OTHER PUBLICATIONS

R. Wisastra and F. J. Dekker (2014). Inflammation, cancer and oxidative lipoxygenase activity are intimately linked. Cancers. (Basel) 6(3): 1500-1521.
D. Poeckel and C. D. Funk (2010). The 5-lipoxygenase/leukotriene pathway in preclinical models of cardiovascular disease. Cardiovascular Research 86: 243-253.
U. S. Akula and B. Odhav (2008). In vitro 5-Lipoxygenase inhibition of polyphenolic antioxidants from undomesticated plants of South Africa. Journal of Medicinal Plants Research 2(9): 207-212.
R. M. Mcmillan, and E. R. H. Walker (1992). Designing therapeutically effective 5-lipoxygenase inhibitors. Trends Pharmacol. Sci., 13: 323-330.
G. Leelaprakash, J. Caroline Rose, and S. M. Dass (2012). Invitro anti-inflammatory activity of momordica charantia by inhibition of lipoxygenase enzyme. Int. J Pharm. Pharm. Sci., 4: 148-152.
E.-R. Sailer, L. R. Subramanian, B. Rall, R. F. Hoernlein, H. P.T. Ammon and H. Safayhi (1996). Acetyl-1 1-keto-fl-boswellic acid (AKBA): structure requirements for binding and 5-lipoxygenase inhibitory activity. British Journal of Pharmacology 117: 615-618.
M. Bishnoi, C. S. Patil, A. Kumar and S. K. Kulkarni (2006). Potentiation of antinociceptive effect of NSAIDs by a specific lipooxygenase inhibitor, acetyl 11-keto-beta boswellic acid. Indian Journal of Experimental Biology 44: 128-132.
A. Goel, F. J. Ahmad, R. M.Singh, and G. N. Singh (2009). Anti-inflammatory activity of nanogel formulation of 3-acetyl-11-keto-β-boswellic acid. Pharmacologyonline 3: 311-318.
R. Csuk, A. N. Barthel, R. Schaefer, A. Barthel, and A. Al-Harrasi (2015). Synthesis and antitumor activity of ring a modified 11-keto-β-boswellic acid derivatives. European Journal of Medicinal Chemistry 92: 700-711.
S. Shen, X. Xu, Z. Liu, J. Liu, and L. Hu (2015). Synthesis and structure-activity relationships of boswellic acid derivatives as potent VEGFR-2 inhibitors. Bioorganic & Medicinal Chemistry 23(9): 1982-1993.
H. Safayhi, G. Tiegs, and A. Wendel, (1985). A novel biologically active seleno-organic compound-V: Inhibition by Ebselen (PZ 51) of rat peritoneal neutrophil lipoxygenase. Biochem. Pharmacol., 34: 2691-2694.
H. P. T. Ammon, T. Mack, G. B. Singh, and H. Safayhi, (1991). Inhibition of leukotriene B4 formation in rat peritonealneutrophils by an ethanolic extract of the gum resin exudate of Boswellia serrata. Planta Med., 57: 203-207.
Safayi et al., "5-Kipoxygenase inhibition by acetyl-11-keto-β-boswellic acid (AKBA): structure requirements for binding and 5-kipoxygenase inhibitory activity," Brit. J. of Pharmac. 117, pp. 615-618 (1996).
Li et al., "Anti-Cancer Agents in Medicinal Chemistry Ring A-modified Derivatives from the Natureal Triterpene 3-O-acetyl-11-keto-β-boswellic Acid and their Cytotoxic Activity, "Anti-Cancer Agents in Medicinal Chem. 16 (2016).

* cited by examiner

*Primary Examiner* — Pancham Bakshi
(74) *Attorney, Agent, or Firm* — Richard C. Litman (57) ABSTRACT

A pentacyclic triterpenoidal derivative can include 3,11-dioxo-24(phenyl)-urs-12-en-24-one (4), 24-norurs-12-en-24(phenyl)-3,11-dione (5), 3,11-dioxo-24(Phenyl)-urs-1,12-diene-24-one (6), or 24-nor-urs-1,12-diene-24(phenyl)-3,11-dione (7). The pentacyclic triterpenoidal derivative demonstrates highly potent 5-lipoxygenase inhibition activity.

11 Claims, 3 Drawing Sheets

PENTACYCLIC TRITERPENOIDAL DERIVATIVES

TECHNICAL FIELD

The present subject matter relates to derivatives of 11-keto-β-boswellic acid, in particular, to certain pentacyclic triterpenoidal derivatives of 11-keto-β-boswellic acid with highly-potent 5-lipoxygenase inhibitor activity, and methods of producing such compounds.

BACKGROUND

Inflammation can be effectively controlled by inhibiting the formation of inflammatory mediators like eicosanoids such as prostaglandins, thromboxanes, and leukotrienes. The formation of such eicosanoids, by oxidation of arachidonic acid released from cell membranes, is mediated by cyclooxygenase (COX) and lipoxygenase (LOX) enzymes. The search for inhibitors of COX and LOX enzymes, to suppress formation of inflammatory mediators, is the basis for developing certain new anti-inflammatory agents. However, recent studies revealed that COX inhibitors causes side effects, especially those leading to cardiovascular problems. The alternative pathway mediated by 5-lipoxygenase has thus become an important target for the development of anti-inflammatory drugs.

5-Lipoxygenase is an important enzyme in the biosynthesis of leukotriene. 5-Lipoxygenase inhibitors bind to the 5-Lipoxygenase enzyme, interrupting leukotriene formation. Leukotriene is the main mediator for a variety of inflammation and hypersensitivity related human diseases, including, but not limited to, arthritis, asthma, and bowel-complication syndromes such as ulcerative colitis and Crohn's disease. Leukotriene also is responsible for certain circulatory disorders, for example, shock and myocardial ischemia.

In this respect, many efforts have been undertaken to isolate natural lipoxygenase inhibitors. For example, some have focused on pentacyclic triterpenoidal frameworks for 5-lipoxygenase inhibitors. Others have focused efforts on chemical alterations of these molecules, attempting to increase their activity as a 5-lipoxygenase inhibitor. 11-keto-β-boswellic acid—a pentacyclic triterpene molecule plant product—has been found to inhibit 5-lipoxygenase via an enzyme-directed, non-competitive mechanism, binding to a pentacyclic triterpene-selective effector site.

Thus, it would be desirable to synthesize and identify additional potent pentacyclic triterpenoidal derivatives for inhibiting 5-lipoxygenase. Such derivatives may prove useful in treating various diseases and adverse health conditions.

SUMMARY

A pentacyclic triterpenoidal derivative can include 3,11-dioxo-24(phenyl)-urs-12-en-24-one (4), having the following structural formula:

4

24-norurs-12-en-24(phenyl)-3,11-dione (5), having the following structural formula:

5

3,11-dioxo-24(Phenyl)-urs-1,12-diene-24-one (6), having the following structural formula:

6 or

24-nor-urs-1,12-diene-24(phenyl)-3,11-dione (7), having the following structural formula:

A method of synthesizing pentacyclic triterpenoidal derivatives from 11-keto-β-boswellic acid can include oxidizing 11-keto-β-boswellic acid (1)

1 with CrO₃-Py complex to obtain the corresponding 3-oxo derivative (2)

2 treating the 3-oxo derivative (2) with thionyl chloride to obtain the corresponding acid chloride (3) (11-diketo-β-boswellic acid chloride)

3

This is followed by a Friedel-Crafts acylation of benzene with the 11-diketo-β-boswellic acid chloride (3) to obtain the corresponding acyl derivative (4):

4 and the corresponding aryl derivative (5):

5

The acyl derivative (4) and aryl derivative (5) can be treated with 2,3-dichloro-5,6-dicyano-p-benzoquinone (DDQ) to produce their respective corresponding $^1\Delta$-enone derivatives, (6) and (7):

7

6

7

Another embodiment of the present subject matter is directed to treating a disease or disorder including administering the compounds (4), (5), (6), or (7) of the present subject matter to a patient in need thereof.

These and other features of the present disclosure will become readily apparent upon further review of the following specification and drawings.

DETAILED DESCRIPTION

A pentacyclic triterpenoidal derivative can include 3,11-dioxo-24(phenyl)-urs-12-en-24-one (4), having the following structural formula:

or,
24-norurs-12-en-24(phenyl)-3,11-dione (5), having the following structural formula:

3,11-dioxo-24(Phenyl)-urs-1,12-diene-24-one (6), having the following structural formula:

24-nor-urs-1,12-diene-24(phenyl)-3,11-dione (7), having the following structural formula:

, or a pharmaceutically acceptable salt of Compound 4, Compound 5, Compound 6, or Compound 7.

The pentacyclic triterpenoidal derivatives can effectively inhibit 5-Lipoxygenase (or "5-LOX") activity. Lipoxygenase inhibitors bind to 5-Lipoxygenase, interrupting leukotriene formation. Leukotriene is the main mediator for a variety of inflammation and hypersensitivity-based human diseases and conditions, including, but not limited to, arthritis, asthma, and bowel-complication syndromes such as ulcerative colitis and Crohn's disease. Leukotriene can also be responsible for circulatory disorders, such as shock and myocardial ischemia. In this context, the pentacyclic triterpenoidal derivatives effectively inhibit 5-LOX activity and can be useful in treating inflammation and hypersensitivity-based diseases, as well as circulatory disorders.

Figure 1:
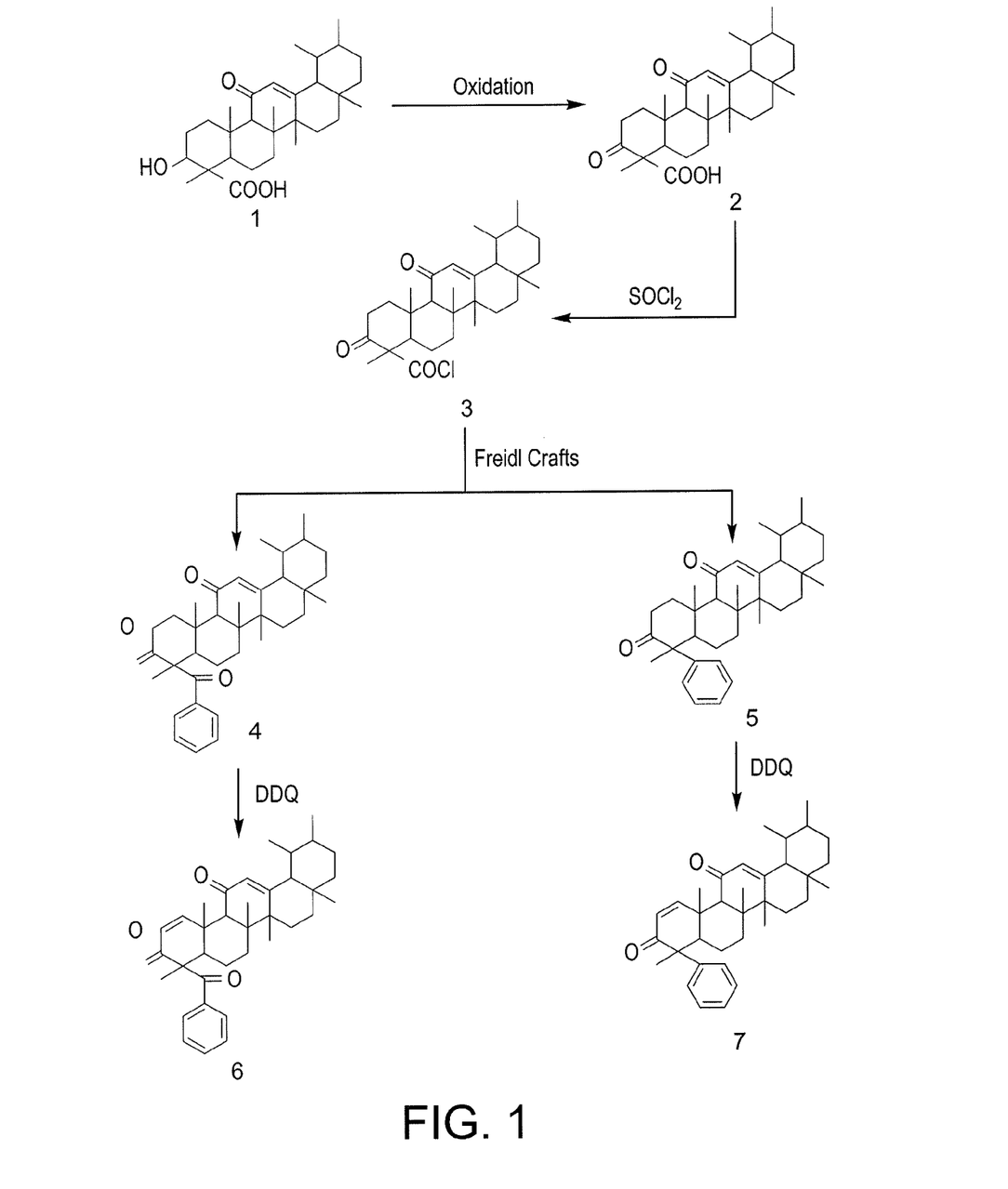
FIG. 1 shows a reaction scheme for synthesizing the pentacyclic triterpenoidal derivatives according to one embodiment of the present subject matter.

According to one embodiment, pentacyclic triterpenoidal derivatives can be prepared from 11-keto-β-boswellic acid (1) as shown in FIG. 1. In particular, FIG. 1 shows a reaction scheme for synthesizing four different pentacyclic triterpenoidal derivatives (Compounds 4, 5, 6, and 7) from 11-keto-β-boswellic acid. The 11-keto-β-boswellic acid (1) is initially oxidized with $CrO_3$-Py to afford a 3-oxo derivative (2). The 3-oxo derivative (2) can be treated with a chlorinating reagent, e.g., thionyl chloride, to afford the corresponding acid chloride (3). Freidel-crafts acylation of benzene with the acid chloride (3) provides corresponding acyl derivatives (4) and, (5). The acyl derivative (4) and aryl derivative (5) can each be treated (separately) with 2,3-dichloro-5,6-dicyano-p-benzoquinone (DDQ) to obtain corresponding $^1\Delta$-enone derivatives (6) and (7), respectively, having the following structures:

The pentacyclic triterpenoidal derivatives selectively bind to the effector site of the 5-Lipoxygenase and demonstrate enzyme inhibitory activity. In particular, the pentacyclic triterpenes scaffold of 11-keto-β-boswellic acid can facilitate binding to the effector site, and the 11-keto functional group can provide 5-Lipoxygenase inhibitory activity. The hydrophilic moieties of the pentacyclic triterpenoidal derivatives can help facilitate the binding of these new compounds to the effector site of the 5-Lipoxygenase, and increase the planarity of ring A, e.g., by introducing the $^1\Delta$-enone moiety, which achieves structural similarity with corticosteroids.

All of the newly synthesized compounds (4) to (7), shown in FIG. 1, exhibit highly potent 5-lipoxygenase inhibition activity. The 5-Lipoxygenase inhibition activity of each of the compounds increased as their structural similarity with cortisone increased. For example, some of the similarities with cortisone included a polycyclic scaffold and the presence of multi $^1\Delta$-enone centers likely involved in binding with the effector site of the 5-Lipoxygenase via hydrogen bonding. It is further contemplated that the presence of the 3-carbonyl functional group greatly increases the 5-Lipoxygenase inhibition due to the increased hydrogen bond formation with the enzyme effector site, and that the presence of a benzoyl ring at location 24 greatly increases the activity for the same reasons mentioned above. This can explain why compound (4), which contains a carbonyl group, is more active than compound (5), which contains no carbonyl group. The carbonyl group is more likely to form a hydrogen bond with the effector site of the enzyme.

A pharmaceutically acceptable salt includes any non-toxic salt of the pentacyclic triterpenoidal derivatives, which are generally prepared by reacting the free acid with a suitable organic or inorganic base. Examples of such salts include, but are not limited to, acetate, benzenesulfonate, benzoate, bicarbonate, bisulfate, bitartrate, borate, bromide, calcium, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynapthoate, iodide, isothionate, lactate, lactobionate, laurate, malate, maleate, mandelate, mesylate, methylbromide, methyinitrate, methylsulfate, mucate, napsylate, nitrate, oleate, oxalate, pamaote, palmitate, panthothenate, phosphate/diphosphate, polygalacturonate, potassium, salicylate, sodium, stearate, subacetate, succinate, tannate, tartrate, teoclate, tosylate, triethiodide, valerate.

Also provided is a pharmaceutical composition including one or more pentacyclic triterpenoidal derivatives. To prepare the pharmaceutical composition, one or more pentacyclic triterpenoidal derivatives or salt thereof, as the active ingredient, is intimately admixed with a pharmaceutical carrier according to conventional pharmaceutical compounding techniques. Carriers are inert pharmaceutical excipients, including, but not limited to, binders, suspending agents, lubricants, flavorings, sweeteners, preservatives, dyes, and coatings. In preparing compositions in oral dosage form, any of the pharmaceutical carriers known in the art may be employed. For example, for liquid oral preparations, suitable carriers and additives include water, glycols, oils, alcohols, flavoring agents, preservatives, coloring agents and the like; for solid oral preparations, suitable carriers and additives include starches, sugars, diluents, granulating agents, lubricants, binders, disintegrating agents and the like. For parenteral use, the carrier will usually comprise sterile water, though other ingredients, for example, for purposes such as aiding solubility or for preservation, may be included. Injectable suspensions may also be prepared, in which case appropriate liquid carriers, suspending agents and the like may be employed.

The pharmaceutical composition can be administered to a patient in need thereof. The pharmaceutical composition can be administered by any conventional route of administration, including, but not limited to, intravenous, oral, subcutaneous, intramuscular, intradermal and parenteral. Depending on the route of administration, the compositions can be constituted into any form. For example, forms suitable for oral administration include solid forms, such as pills, gel caps, tablets, caplets, capsules (each including immediate release, timed release and sustained release formulations), granules, and powders. Forms suitable for oral administration also include liquid forms, such as solutions, syrups, elixirs, emulsions, and suspensions. In addition, forms useful for parenteral administration include sterile solutions, emulsions and suspensions.

The pentacyclic triterpenoidal derivatives may be used to treat inflammation and/or a circulatory disorder. A therapeutically effective amount of the pentacyclic triterpenoidal derivatives may be determined initially from assays described herein and adjusted for specific desired compositions using routine methods.

For the examples that follow, all melting points are uncorrected and were measured using an electro-thermal capillary melting point apparatus. The IR spectra were recorded on a Shimadzu FT-IR 8101 PC infrared spectrophotometer. The $^1$H-NMR spectra were determined with Bruker AM-200 MHz spectrometer. The chemical shifts are expressed on the $\delta$ (ppm) scale using Tetramethylsilane (TMS) as the standard reference. Mass spectra were recorded on a Finnigan SSQ operating at 70 ev. Elemental analysis was determined on a Perkin Elmer 240 (microanalysis), located at Microanalysis Center, Cairo University, Cairo, Egypt.

The following examples illustrate the present teachings.

Example 1

Synthesis of 3,11-dioxo-urs-12-en-24β-acid chloride (3)

A mixture of 6 g compound (2) and 20 mL thionyl chloride was refluxed for 1 hour. Excess reagent was removed under reduced pressure, and the product was washed with m-hexane to give the corresponding acid chloride (3). This crude acid chloride (3) was crystallized from petroleum ether, yielding the corresponding acid chloride (3) in crystalline form.

Yield 90.4%, mp 244° C., $[\alpha]_D^{25}$=+119 (c 1, petroleum ether). IR (KBr, cm$^{-1}$): 2977 (CH, aliphatic), 1746 (C=O), 1801 (—COCl), 1672, 1628, 1461, 1238 (α,β unsaturated C=O), 1H-NMR (400 MHz, CDCl$_3$, δ in ppm): 0.76 (d, 3H, CH$_3$, H-29), 0.78 (d, 3H, CH$_3$, H-30), 0.92 (s, 3H, CH$_3$, H-28), 1.11 (s, 3H, CH$_3$, H-25), 1.16 (s, 3H, CH$_3$, H-26), 1.20 (m, α-H, CH, H-15), 1.23 (s, 3H, CH$_3$, H-27), 1.25 (m, β-1H, CH, H-21), 1.28 (m, α-1H, CH, H-19), 1.30 (m, β-1H, CH, H-20), 1.33 (s, 3H, CH$_3$, H-23), 1.35 (m, β-1H, CH, H-7), 1.38 (m, β-1H, CH, H-6), 1.40 (dd, 1H, CH, H-5), 1.45 (m, α-1H, CH, H-21), 1.48 (m, α-1H, CH, H-7), 1.51 (d, 1H, CH, H-18), 1.78 (m, α-1H, CH, H-22), 1.80 (m, α-1H, CH, H-6), 1.94 (m, β-1H, CH, H-16), 1.98 (m, β-1H, CH, H-22), 2.07 (t, α-1H, CH, H-16), 2.16 (m, β-H, CH, H-15), 2.40 (s, 1H, CH, H-9), 2.46 (dd, 2H, CH$_2$, H-1), 2.71 (dd, 2H, CH$_2$, H-2), 5.54 (s, 1H, CH, H-12). $^{13}$C NMR (pyridine-d$_5$): δ ppm 34.32 (C-1), 108.36 (C-2), 70.74 (C-3), 47.56 (C-4), 49.27 (C-5), 19.50 (C-6), 31.63 (C-7), 44.71 (C-8), 60.48 (C-9), 37.67 (C-10), 199.88 (C-11), 130.46 (C-12), 165.64 (C-13), 45.73 (C-14), 33.63 (C-15), 27.46 (C-16), 34.71 (C-17), 59.54 (C-18), 39.47 (C-19), 39.67 (C-20), 27.87 (C-21), 41.93 (C-22), 24.47 (C-23), 170.51 (C-24), 13.66 (C-25), 18.77 (C-26), 20.89 (C-27), 21.95 (C-28), 17.48 (C-29), 29.63 (C-30). MS (EI): m/z 487.5 (100%) [M$^+$]. Anal. Calcd for C$_{30}$H$_{44}$ClO$_3$ (487.5): Calcd C, 73.84; H, 9.02; Cl, 7.28. Found C, 73.87; H, 8.92; Cl, 7.20.

Example 2

Synthesis of 3,11-dioxo-24(phenyl)-urs-12-en-24-one (4) and 24-norurs-12-en-24(phenyl)-3,11-dione (5)

A mixture of dry benzene (30 mL) and anhydrous aluminum chloride (1.5 g) were placed in three neck round bottom flasks provided with a separator funnel. The flask was cooled in a cold water bath (5° C.). Through the separator funnel at one side neck of the flask, compound (3) (4.38 g, 9 mmol) dissolved in benzene (50 mL) was added slowly over a ½ hour period with continuous mechanical stirring using a vertical motor shaft. The reaction was then heated in a water bath at 60° C. for 1 h, then cooled and poured over ice (100 g), followed by addition of concentrated hydrochloric acid (10 mL). The benzene layer was separated and dried over anhydrous sodium sulfate, and then evaporated until dry, resulting in compounds (4) and (5). Compound (4) was separated from compound (5) using medium pressure chromatography.

3,11-Dioxo-24(Phenyl)-urs-12-en-24-one (4): Yield 74%, mp 300° C., $[\alpha]_D^{25}$=+179 (c 1, MeOH). IR (KBr, cm$^{-1}$): 3048 (CH, aromatic), 2981 (CH, aliphatic), 1746 (C=O), 1731 (—CO), 1670, 1628, 1457, 1236 ($\alpha,\beta$ unsaturated C=O). $^1$H-NMR (400 MHz, CDCl$_3$, δ in ppm): 0.74 (d, 3H, CH$_3$, H-29), 0.78 (d, 3H, CH$_3$, H-30), 0.92 (s, 3H, CH$_3$, H-28), 1.13 (s, 3H, CH$_3$, H-25), 1.17 (s, 3H, CH$_3$, H-26), 1.20 (m, α-H, CH, H-15), 1.25 (s, 3H, CH$_3$, H-27), 1.27 (m, α-1H, CH, H-21), 1.29 (m, α-1H, CH, H-19), 1.31 (m, β-1H, CH, H-20), 1.34 (s, 3H, CH$_3$, H-23), 1.37 (m, β-1H, CH, H-7), 1.40 (m, β-1H, CH, H-6), 1.44 (dd, 1H, CH, H-5), 1.49 (m, α-1H, CH, H-21), 1.53 (d, 1H, CH, H-18), 1.57 (m, α-1H, CH, H-7), 1.80 (m, α-1H, CH, H-22), 1.84 (m, α-1H, CH, H-6), 1.91 (m, β-1H, CH, H-16), 2.01 (m, β-1H, CH, H-22), 2.11 (t, α-1H, CH, H-16), 2.19 (m, β-H, CH, H-15), 2.39 (s, 1H, CH, H-9), 2.45 (dd, 2H, CH$_2$, H-1), 2.73 (dd, 2H, CH$_2$, H-2), 5.53 (s, 1H, CH, H-12), 7.21-7.38 (m, 5H, Ar—H). $^{13}$C NMR (pyridine-d$_5$): δ ppm 34.35 (C-1), 108.55 (C-2), 70.60 (C-3), 47.70 (C-4), 49.62 (C-5), 19.33 (C-6), 31.35 (C-7), 44.48 (C-8), 60.88 (C-9), 37.78 (C-10), 199.79 (C-11), 130.89 (C-12), 165.58 (C-13), 45.26 (C-14), 33.57 (C-15), 27.66 (C-16), 34.82 (C-17), 59.92 (C-18), 39.10 (C-19), 39.70 (C-20), 27.51 (C-21), 41.56 (C-22), 24.80 (C-23), 199.99 (C-24), 13.60 (C-25), 18.79 (C-26), 20.90 (C-27), 21.60 (C-28), 17.71 (C-29), 29.83 (C-30), 137.20, 126.70, 126.00, 132.80 (6C, Ar—C). MS (EI): m/z 528 (71%) [M$^+$]. Anal. Calcd for C$_{36}$H$_{48}$O$_3$ (528): Calcd C, 81.81; H, 9.09. Found C, 81.80; H, 9.10.

24-Norurs-12-en-24(phenyl)-3,11-dione (5): Yield 22%, mp 256° C., $[\alpha]_D^{25}$=+112 (c 1, MeOH). IR (KBr, cm$^{-1}$): 3051 (CH, aromatic), 2983 (CH, aliphatic), 1746 (C=O), 1670, 1629, 1451, 1236 ($\alpha,\beta$ unsaturated C=O). $^1$H-NMR (400 MHz, CDCl$_3$, δ in ppm): 0.73 (d, 3H, CH$_3$, H-29), 0.78 (d, 3H, CH$_3$, H-30), 0.93 (s, 3H, CH$_3$, H-28), 1.13 (s, 3H, CH$_3$, H-25), 1.18 (s, 3H, CH$_3$, H-26), 1.20 (m, α-H, CH, H-15), 1.24 (s, 3H, CH$_3$, H-27), 1.27 (m, β-1H, CH, H-21), 1.29 (m, α-1H, CH, H-19), 1.31 (m, β-1H, CH, H-20), 1.34 (s, 3H, CH$_3$, H-23), 1.38 (m, —1H, CH, H-7), 1.42 (m, β-1H, CH, H-6), 1.45 (dd, 1H, CH, H-5), 1.48 (m, α-1H, CH, H-21), 1.53 (d, 1H, CH, H-18), 1.58 (m, α-1H, CH, H-7), 1.80 (m, α-1H, CH, H-22), 1.86 (m, α-1H, CH, H-6), 1.91 (m, β-1H, CH, H-16), 2.04 (m, β-1H, CH, H-22), 2.11 (t, α-1H, CH, H-16), 2.21 (m, β-H, CH, H-15), 2.38 (s, 1H, CH, H-9), 2.46 (dd, 2H, CH$_2$, H-1), 2.76 (dd, 2H, CH$_2$, H-2), 5.53 (s, 1H, CH, H-12). 7.17-7.25 (m, 5H, Ar—H). $^{13}$C NMR (pyridine-d$_5$): δ ppm 34.45 (C-1), 108.61 (C-2), 70.58 (C-3), 29.69 (C-4), 49.60 (C-5), 19.34 (C-6), 31.36 (C-7), 44.47 (C-8), 60.87 (C-9), 37.79 (C-10), 199.81 (C-11), 130.92 (C-12), 165.58 (C-13), 45.30 (C-14), 33.66 (C-15), 27.67 (C-16), 34.85 (C-17), 59.94 (C-18), 39.15 (C-19), 39.75 (C-20), 27.52 (C-21), 41.53 (C-22), 24.84 (C-23), 13.64 (C-25), 18.60 (C-26), 20.96 (C-27), 21.69 (C-28), 17.74 (C-29), 29.84 (C-30), 150.82, 125.14, 128.10, 125.48 (6C, Ar—C). MS (EI): m/z 500 (100%) [M$^+$]. Anal. Calcd for C$_{35}$H$_{48}$O$_2$ (500): Calcd C, 84.00; H, 9.60. Found C, 84.00; H, 9.90.

Example 3

Synthesis of 3,11-dioxo-24(Phenyl)-urs-1,12-diene-24-one (6) and 24-nor-urs-1,12-diene-24(phenyl)-3,11-dione (7)

A solution of the appropriate 3-keto derivative (4) or (5) (1.42 mmol), 2,3-dichloro-5,6-dicyano-p-benzoquinone (DDQ) (0.36 g) and P-toluene sulphonic acid (PTSA) (0.6 g) in dry benzene (10 mL) was refluxed for 5 hours. The obtained orange solution was percolated over alumina in a small Buchner funnel and it was evaporated to dryness to give a white precipitate. The precipitated product was purified with medium pressure chromatography to give products (6) or (7), respectively.

11-Dioxo-24(Phenyl)-urs-1,12-diene-24-one (6): Yield 61%, mp 224° C., $[\alpha]_D^{25}$=+71 (c 1, MeOH). IR (KBr, cm$^{-1}$): 3045 (CH, aromatic), 2977 (CH, aliphatic), 1744 (C=O), 1734 (CO), 1658 (C=O, enone), 1671, 1621, 1451, 1231 ($\alpha,\beta$ unsaturated C=O). $^1$H-NMR (400 MHz, CDCl$_3$, δ in ppm): 0.74 (d, 3H, CH$_3$, H-29), 0.77 (d, 3H, CH$_3$, H-30), 0.91 (s, 3H, CH$_3$, H-28), 1.13 (s, 3H, CH$_3$, H-25), 1.16 (s, 3H, CH$_3$, H-26), 1.21 (m, α-H, CH, H-15), 1.23 (s, 3H, CH$_3$, H-27), 1.26 (m, 1-1H, CH, H-21), 1.29 (m, α-1H, CH, H-19), 1.32 (m, β-1H, CH, H-20), 1.35 (s, 3H, CH$_3$, H-23), 1.39 (m, β-1H, CH, H-7), 1.44 (m, β-1H, CH, H-6), 1.48 (dd, 1H, CH, H-5), 1.52 (m, α-1H, CH, H-21), 1.55 (d, 1H, CH, H-18), 1.59 (m, α-1H, CH, H-7), 1.81 (m, α-1H, CH, H-22), 1.85 (m, α-1H, CH, H-6), 1.94 (m, β-1H, CH, H-16), 2.01 (m, 3-1H, CH, H-22), 2.09 (t, α-1H, CH, H-16), 2.19 (m, β-H, CH, H-15), 2.39 (s, 1H, CH, H-9), 5.53 (s, 1H, CH, H-12), 5.72 (d, 1H, CH, H-2), 6.72 (d, 1H, CH, H-1), 7.21-7.38 (m, 5H, Ar—H). $^{13}$C NMR (pyridine-d$_5$): δ ppm 40.41 (C-1), 174.60 (C-2), 70.63 (C-3), 47.74 (C-4), 49.62 (C-5), 19.35 (C-6), 31.38 (C-7), 44.44 (C-8), 60.88 (C-9), 37.66 (C-10), 199.87 (C-11), 130.54 (C-12), 165.58 (C-13), 45.54 (C-14), 33.33 (C-15), 27.33 (C-16), 34.82 (C-17), 59.55 (C-18), 39.33 (C-19), 39.70 (C-20), 27.51 (C-21), 41.56 (C-22), 24.57 (C-23), 199.64 (C-24), 13.33 (C-25), 18.75 (C-26), 20.96 (C-27), 21.67 (C-28), 17.77 (C-29), 29.84 (C-30), 137.23, 126.75, 126.05, 132.84 (6C, Ar—C). MS (EI): m/z 526 (100%) [M$^+$]. Anal. Calcd for C$_{36}$H$_{46}$O$_3$ (526): Calcd C, 82.12; H, 8.74. Found C, 82.20; H, 8.75.

24-Nor-urs-1,12-diene-24(phenyl)-3,11-dione (7): Yield 72%, mp 267° C., $[\alpha]_D^{25}$=+98 (c 1, MeOH). IR (KBr, cm$^{-1}$): 3051 (CH, aromatic), 2983 (CH, aliphatic), 1659 (C=O, enone), 1746 (C=O), 1670, 1629, 1451, 1236 ($\alpha,\beta$ unsaturated C=O). $^1$H-NMR (400 MHz, CDCl$_3$, δ in ppm): 0.71 (d, 3H, CH$_3$, H-29), 0.74 (d, 3H, CH$_3$, H-30), 0.90 (s, 3H, CH$_3$, H-28), 1.11 (s, 3H, CH$_3$, H-25), 1.15 (s, 3H, CH$_3$, H-26), 1.18 (m, α-H, CH, H-15), 1.21 (s, 3H, CH$_3$, H-27), 1.25 (m, β-H, CH, H-21), 1.28 (m, α-1H, CH, H-19), 1.30 (m, β-1H, CH, H-20), 1.33 (s, 3H, CH$_3$, H-23), 1.36 (m, β-1H, CH, H-7), 1.41 (m, β-1H, CH, H-6), 1.45 (dd, 1H, CH, H-5), 1.48 (m, α-1H, CH, H-21), 1.55 (d, 1H, CH, H-18), 1.59 (m, α-1H, CH, H-7), 1.80 (m, α-1H, CH, H-22), 1.86 (m, α-1H, CH, H-6), 1.91 (m, β-1H, CH, H-16), 2.04 (m, β-1H, CH, H-22), 2.11 (t, α-1H, CH, H-16), 2.21 (m, 3-H, CH, H-15), 2.38 (s, 1H, CH, H-9), 5.53 (s, 1H, CH, H-12), 5.72 (d, 1H, CH, H-2), 6.72 (d, 1H, CH, H-1), 7.17-7.25 (m, 5H, Ar—H). $^{13}$C NMR (pyridine-d$_5$): δ ppm 40.45 (C-1), 174.65 (C-2), 70.67 (C-3), 29.76 (C-4), 49.78 (C-5), 19.90 (C-6), 31.87 (C-7), 44.55 (C-8), 60.56 (C-9), 37.8079 (C-10), 199.90 (C-11), 131.09 (C-12), 165.67 (C-13), 45.45 (C-14), 33.78 (C-15), 27.70 (C-16), 34.90 (C-17), 59.89 (C-18), 39.22 (C-19), 39.67 (C-20), 27.60 (C-21), 41.58 (C-22), 24.91 (C-23), 13.70 (C-25), 18.74 (C-26), 21.00 (C-27), 21.70 (C-28), 17.83 (C-29), 29.78 (C-30), 150.77, 125.18, 128.11, 125.55 (6C, Ar—C). MS (EI): m/z 498 (100%) [M$^+$]. Anal. Calcd for C$_{35}$H$_{46}$O$_2$ (498): Calcd C, 84.33; H, 9.23. Found C, 84.30; H, 9.30.

Example 4

Rat Peritoneal PMNL and Subcellular Fractionation

Glycogen-elicited rat peritoneal PMNL were collected 4 hours after the injection of a glycogen solution (5%) in Dulbecco's phosphate-buffered saline (PBS) into the peritoneum of 300-350 g Wistar rats. The washed cells (>90% PMNL) were lysed at $2\times10^7$ cells $mL^{-1}$ by sonication (3×5 s, digital Sonifier) in PBS containing 1 mm EDTA, and were subjected to sequential centrifugation at 10,000 and 105,000 g for 10 and 60 min (4° C.), respectively. Freshly obtained PMNL suspensions and aliquots of the 105,000 g supernatants were assayed for 5-lipoxygenase activity.

Example 5

5-Lipoxygenase Assay

For 5-lipoxygenase product formation from endogenous arachidonic acid, glycogen-elicited rat peritoneal PMNL ($1\times10^7$ cells) were stimulated at 37° C. for 5 min by ionophore A23187 and $Ca^{2+}$. The 5-lipoxygenase activity in the cell-free system was tested in aliquots (corresponding to $1\times10^7$ cells) of the 105,000 g supernatant fraction of rat PMNL in the presence of 1 mm ATP, 1.8 mM $CaCl_2$, 1 mM EDTA, and 20 μM arachidonic acid at 37° C. for 5 min. In both intact cells and cell-free tests, the incubations were terminated by cooling to 4° C. and acidification to pH of 3 with formic acid. For inhibition studies, the test compounds dissolved in dimethyl sulphoxide (DMSO) were added 5 min prior to initiation.

Inhibitors and non-inhibitory pentacyclic triterpenes were added simultaneously. All incubations, including controls, were carried out in the presence of 0.5% DMSO. The 5-lipoxygenase products were quantified after the addition of 170 ng $PGB_2$ as an internal standard by extraction, with RP-HPLC separation and ultraviolet detection of products. With intact rat PMNL and the 105,000 g supernatant fraction the main products from arachidonic acid of 5 min incubations were leukotriene $B_4$ ($LTB_4$), 6-trans-$LTB_4$, 12-epi-6-trans-$LTB_4$ and 5-HETE along with negligible amounts of 5(S), 12(S)-diHETE. The formation of co-oxidized metabolites from $LTB_4$ was observed with intact cells only if the incubations were carried out for longer than 5 min.

Example 6

5-Lipoxygenase Inhibitory Activity

Figure 2:
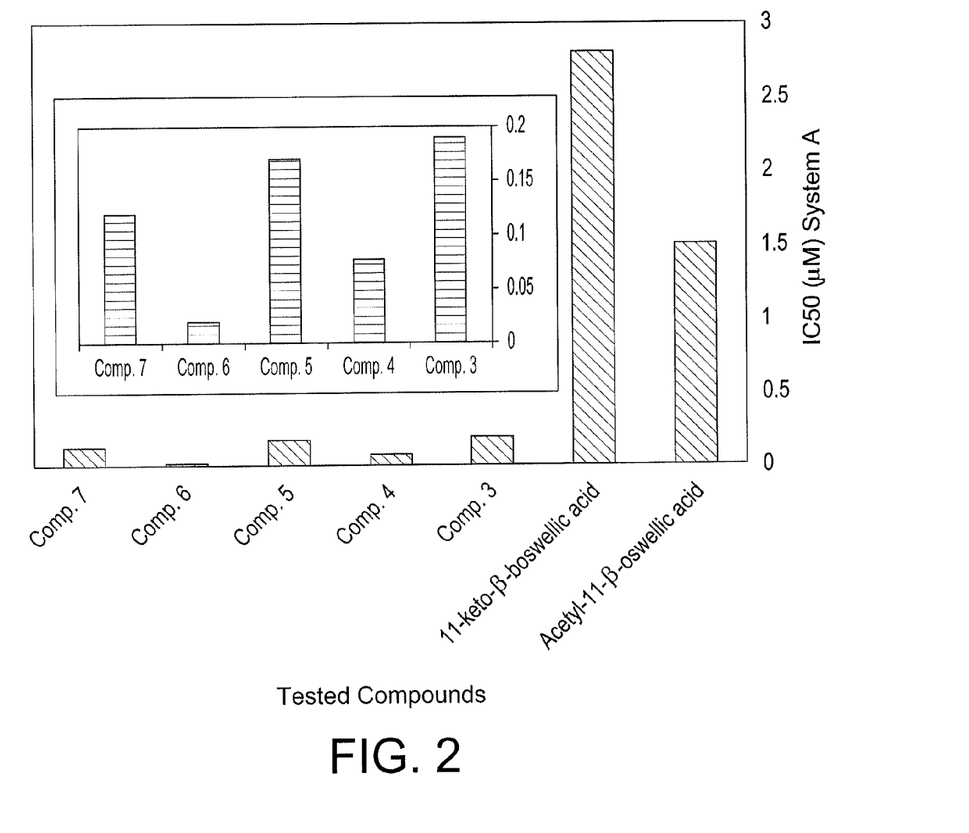
FIG. 2 is a graph showing the inhibition effects of the synthesized compounds on 5-LOX product formation (in System A, using intact cells as described further below).
Figure 3:
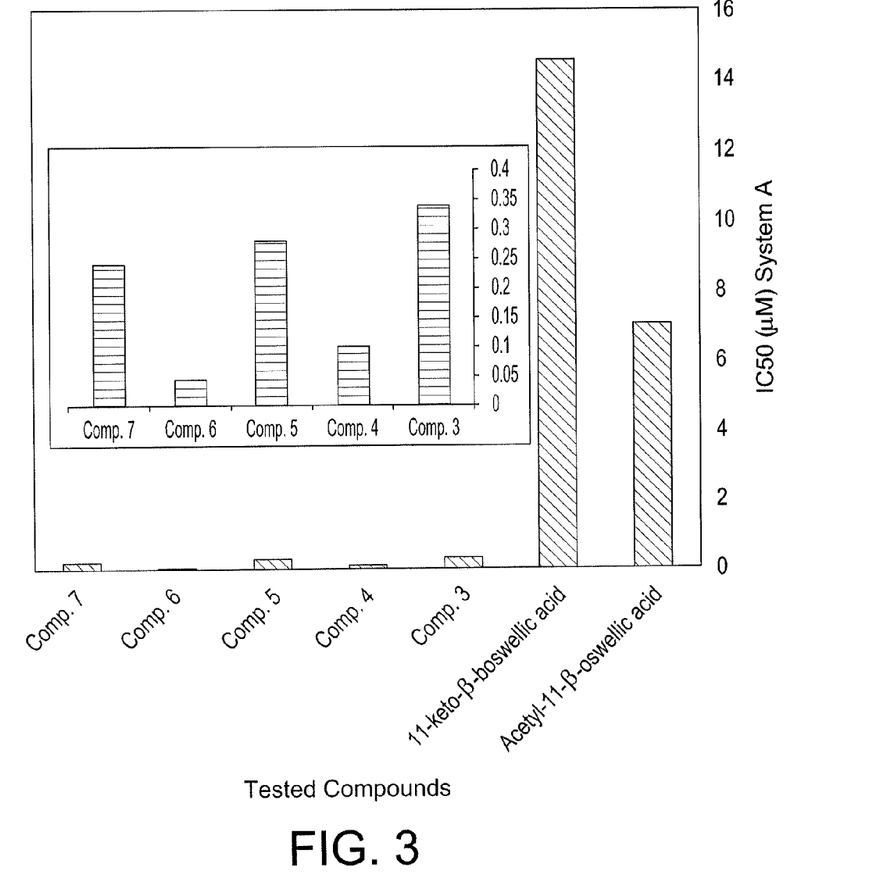
FIG. 3 is a graph showing the inhibition effects of the synthesized compounds on 5-LOX product formation (in System B, a cell-free environment as described further below).

Table 1 shows the effects of newly synthesized pentacyclic triterpenoidal derivatives on 5-LOX product formation (i.e., the sum of 5, 12-diHETES plus 5-HETE) from endogenous arachidonic acid in ionophore-stimulated intact rat polymorphonuclear leukocytes (PMNL) (System A) and from 20 μM exogenous substrate in 105.000 g supernatants of rat PMNL (System B). FIG. 2 is a graph showing the effects of the pentacyclic triterpenoidal derivatives on 5-Lox product formation for System A. FIG. 3 is a graph showing the effects of the pentacyclic triterpenoidal derivatives on 5-Lox product formation for System B. Inhibition concentrations ($IC_{50}$) of the biological effect of each of the compounds were determined after logit-log transformation of the data for each experiment. Data of independent observations (n=6) are shown as means±standard deviation.

TABLE 1

| Comp. Name/No. | $IC_{50}$ (μM) System A | $IC_{50}$ (μM) System B |
| --- | --- | --- |
| AKBA | 1.5 ± 0.2 | 7 ± 2.2 |
| 11-keto-β-boswellic acid/1 | 2.8 ± 0.2 | 14.6 ± 7.6 |

TABLE 1-continued

| Comp. Name/No. | $IC_{50}$ (μM) System A | $IC_{50}$ (μM) System B |
| --- | --- | --- |
| 3 | 0.19 ± 0.02 | 0.34 ± 0.07 |
| 4 | 0.078 ± 0.006 | 0.098 ± 0.004 |
| 5 | 0.17 ± 0.01 | 0.28 ± 0.03 |
| 6 | 0.021 ± 0.003 | 0.044 ± 0.002 |
| 7 | 0.12 ± 0.01 | 0.24 ± 0.03 |

Acetyl-11-keto-β-boswellic acid (AKBA, in Table 1) inhibited 5-Lipoxygenase activity in intact cells (System A: $IC_{50}$=1.5 μM) and in the cell-free system (System B: $IC_{50}$=7 μM). 11-Keto-β-boswellic acid (1) also inhibited 5-Lipoxygenase activity in both intact cells and the cell-free system ($IC_{50}$=2.8 μM and 14.6 μM, respectively). When compound (1) was converted to the 3-oxo analogue (2) and then the corresponding acid chloride (3), the inhibition activity increased ($IC_{50}$=0.19 μM and 0.34 μM for compound (3)).

Converting compound (3) into compounds (4) ($IC_{50}$=0.078 μM and 0.098 μM for Systems A and B, respectively) and (5) ($IC_{50}$=0.17 μM and 0.28 μM, Systems A and B, respectively) greatly increased the inhibition activity. It is believed that the inhibition activity of compound (4) was larger than compound (5) due to its carbonyl function at position 24, which is capable of forming extra hydrogen bonds with the effector 5-Lipoxygenase binding site.

Converting compounds (4) and (5) to compounds (6) ($IC_{50}$=0.021 μM and 0.044 μM, Systems A and B, respectively) and (7) ($IC_{50}$=0.12 μM and 0.24 μM, Systems A and B, respectively), respectively, greatly increased the inhibition activity. It is believed that the increase can be attributed to increased structural similarity with cortisone.

It is to be understood that the present subject matter is not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

We claim:

1. A pentacyclic triterpenoidal derivative compound selected from the group consisting of:

Compound 4, having following structural formula

4

Compound 5, having the following structural formula

5

Compound 6, having the following structural formula

6 and
Compound 7, having the following structural formula

7 a pharmaceutically acceptable salt thereof.

2. The pentacyclic triterpenoidal derivative of claim 1, wherein the compound is Compound 4.

3. A pharmaceutical composition, comprising the compound of claim 2 and a pharmaceutically acceptable carrier.

4. The pentacyclic triterpenoidal derivative of claim 1, wherein the compound is Compound 5.

5. A pharmaceutical composition, comprising the compound of claim 4 and a pharmaceutically acceptable carrier.

6. The pentacyclic triterpenoidal derivative of claim 1, wherein the compound is Compound 6.

7. A pharmaceutical composition, comprising the compound of claim 6 and a pharmaceutically acceptable carrier.

8. The pentacyclic triterpenoidal derivative of claim 1, wherein the compound is Compound 7.

9. A pharmaceutical composition, comprising the compound of claim 8 and a pharmaceutically acceptable carrier.

10. A method of preparing a pentacyclic triterpenoidal derivative, comprising
  oxidizing 11-keto-β-boswellic acid with $CrO_3$-Py to provide a corresponding 3-oxo derivative;
  treating the 3-oxo derivative with a chlorinating agent to provide 11-diketo-β-boswellic acid chloride;
  acylating a benzene with the 11-diketo-β-boswellic acid chloride to provide pentacyclic triterpenoidal derivatives, the pentacyclic triterpenoidal derivatives including
Compound 4, having the structural formula

4 and
Compound 5, having the structural formula

5

11. The method of claim 10, further comprising:
  treating at least one of Compounds 4 and 5 with 2,3-dichloro-5,6-dicyano-p-benzoquinone to provide pen- tacyclic triterpenoidal derivatives, the pentacyclic triterpenoidal derivatives including at least one of
Compound 6, having the structural formula

6 and

Compound 7, having the structural formula

7

* * * * *